(12) United States Patent
Schobben et al.

(10) Patent No.: US 11,318,319 B2
(45) Date of Patent: May 3, 2022

(54) IMPLANTABLE STIMULATOR WITH A CONFORMABLE FOIL-LIKE ELECTRODE ARRAY

(71) Applicant: Salvia BioElectronics B.V., Eindhoven (NL)

(72) Inventors: Daniel Willem Elisabeth Schobben, Eindhoven (NL); Hubert Cecile Francois Martens, Eindhoven (NL)

(73) Assignee: Salvia BioElectronics B.V., Eindhoven (NL)

( * ) Notice: Subject to any disclaimer, the term of this patent is extended or adjusted under 35 U.S.C. 154(b) by 184 days.

(21) Appl. No.: 16/703,706

(22) Filed: Dec. 4, 2019

(65) Prior Publication Data

US 2021/0170182 A1    Jun. 10, 2021

(51) Int. Cl.
*A61N 1/375* (2006.01)
*A61N 1/36* (2006.01)

(52) U.S. Cl.
CPC ......... *A61N 1/375* (2013.01); *A61N 1/36007* (2013.01); *A61N 1/36064* (2013.01); *A61N 1/36075* (2013.01)

(58) Field of Classification Search
CPC .......................... A61N 1/36075; A61N 1/0526
(Continued)

(56) References Cited

U.S. PATENT DOCUMENTS 9,168,719 B2   10/2015 Tam
2005/0266219 A1   12/2005 Hodgson
(Continued)

FOREIGN PATENT DOCUMENTS

WO    2002/096482 A2    12/2002
WO    2015/107515 A1    7/2015
WO    2016/033369 A1    3/2016

OTHER PUBLICATIONS

Vajari D Ashouri et al: "Hybrid multimodal Deep Brain probe (DBS array) for advanced brain research", 2015 7TH International IEEE/EMBS Conference On Neural Engineering (NER), IEEE, Apr. 22, 2015 [Apr. 22, 2015], pp. 280-283, XP033166214, DOI: 10.1109/NER.2015.7146614.

(Continued)

*Primary Examiner* — Amanda K Hulbert
*Assistant Examiner* — Philip C Edwards
(74) *Attorney, Agent, or Firm* — Fresh IP PLC; Clifford D. Hyra; Aubrey Y Chen

(57) ABSTRACT

An implantable stimulator is provided having a conformable foil-like substrate, having a longitudinal axis extending from a pulse generator to a distal end of the substrate. The substrate comprising one or more adjacent polymeric substrate layers and an electrode array. The electrode array having a first and second electrode where one or more electrical interconnections are comprised in the substrate. The conformable foil-like substrate has a maximum thickness of 0.5 millimeter or less, proximate the electrodes. By providing a more easily patternable multilayer substrate, more complicated electrode array configurations may be supported, allowing a higher degree of flexibility to address transverse and/or longitudinal misalignment. By providing a relatively thin implantable electrode array user comfort may be increased through application of energy to tissue by the implantable stimulator.

21 Claims, 6 Drawing Sheets

(58) Field of Classification Search
USPC .......................................................... 607/1
See application file for complete search history.

(56) References Cited

U.S. PATENT DOCUMENTS

| | | |
|---|---|---|
| 2006/0173497 A1 | 8/2006 | Meeh |
| 2007/0073356 A1 | 3/2007 | Rooney |
| 2007/0128420 A1 | 6/2007 | Maghribi |
| 2007/0264303 A1 | 11/2007 | Atanasoska |
| 2008/0015669 A1 | 1/2008 | Jolly |
| 2010/0057165 A1 | 4/2010 | Moffitt |
| 2010/0148345 A1* | 6/2010 | Eckhardt ............ H01L 21/76898 257/690 |
| 2011/0015686 A1 | 1/2011 | Kara |
| 2011/0093043 A1 | 4/2011 | Torgerson |
| 2012/0172653 A1 | 7/2012 | Chornenky |
| 2012/0296444 A1 | 11/2012 | Greenberg |
| 2012/0323288 A1* | 12/2012 | Anderson ............ A61N 1/0531 607/3 |
| 2013/0030510 A1 | 1/2013 | Han |
| 2014/0031889 A1* | 1/2014 | Mashiach .......... A61B 17/0482 607/42 |
| 2015/0142083 A1 | 5/2015 | Yomtov |
| 2016/0067477 A1 | 3/2016 | Advanced |
| 2016/0166828 A1 | 6/2016 | Yu |
| 2017/0072200 A1 | 3/2017 | Fletcher |
| 2018/0093096 A1 | 4/2018 | Mashiach |
| 2018/0117332 A1 | 5/2018 | Robinson |
| 2019/0059820 A1 | 2/2019 | Schuettler |

OTHER PUBLICATIONS

Search Report for NL Patent Application NL2025268 dated Nov. 26, 2020.
International Search Report for Application PCT/IB2020/061474 dated Mar. 29, 2021.
Notice of Allowance and Fees Due, dated May 26, 2021, issued in U.S. Appl. No. 17/016,426; 7 pages.
Notice of Allowance and Fees Due, dated Apr. 14, 2021, issued in U.S. Appl. No. 17/016,426; 7 pages.
Hassler, Boretius, Steglitz, Polymers for neural implants, Journal of Polymer Science Part B: Polymer Physics/ vol. 49, Iss. 1, online, Nov. 23, 2010, 10.1002/polb.22169.
Hoang, Chung, Elias, Irreversible bonding of polyimide and polydimethylsiloxane (PDMS) based on a thiol-epoxy click reaction, Journal of Micromechanics and Microengineering, online, Sep. 19, 2016, 10.1088/0960-1317/26/U.S. Appl. No. 10/105,019.
Lonys, Vanhoestenberghe, Julemont, Godet, Delplancke, Mathys, Nonclercq, Silicone rubber encapsulation for an endoscopically implantable gastrostimulator, Med. Biol. Eng. Comput. 53 319-29, online, Jan. 6, 2015, 10.1007/s11517-014-1236-9.
Donaldson, Lamont, Shah, Mentink, Perkins, Apparatus to investigate the insulation impedance and accelerated life-testing of neural interfaces, J. Neural Eng. 15 (2018) 066034 (23pp), online, Sep. 4, 2018, 10.1088/1741-2552/aadeac.
Li, Turunen, Niiranen, Chen, Paulasto-Krockel, A reliability study of adhesion mechanism between liquid crystal polymer and silicone adhesive, Microelectronics Reliability 52 (2012) 2962-2969, online, Aug. 21, 2012, 10.1016/j microreL2012.07.027.
Song, Li, Rogers, Barrier materials for flexible bioelectronic implants with chronic stability—Current approaches and future directions, APL Mater. 7, 050902 (2019), online, May 21,2019, 10.1063/1.5094415.
Ahn, Jeong, Kim, Emerging Encapsulation Technologies for Long-Term Reliability of Microfabricated Implantable Devices, Micromachines 2019,10, 508, online, Jul. 31, 2019, 10.3390/mi10080508.
Li, Cauwe, Yang, Schaubroeck, Mader, Op De Beeck, Ultra-Long-Term Reliable Encapsulation Using an Atomic Layer Deposited Hf02/AI203/Hf02 Triple-Interlayer for Biomedical Implants, Coatings 2019, 9, 579, online, Sep. 12, 2019, 10.3390/coatings9090579.
Schaubroeck, Verplancke, Cauwe, Cuypers, Baumans, Op De Beeck, Polyimide-ALD-Polyimide layers as hermetic encapsulant for implant, XXXI International Conference on Surface Modification Technologies (SMT31), Mons Belgium, 2017-07-05.
Non-Final Office Action dated Feb. 3, 2021, issued in U.S. Appl. No. 17/016,426; 7 pages.

* cited by examiner

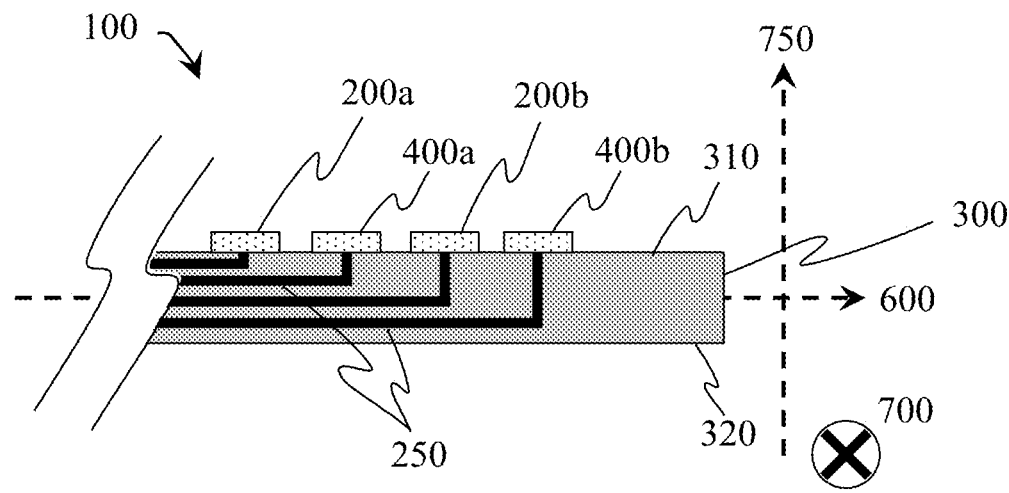
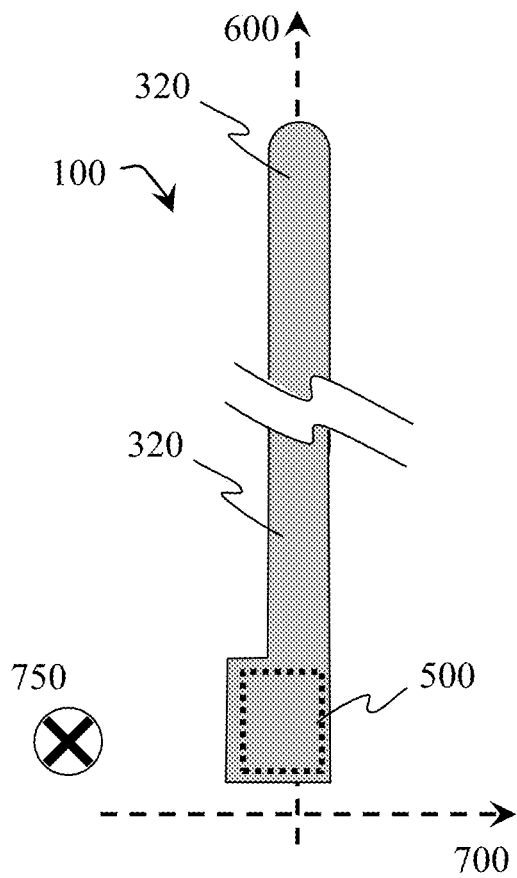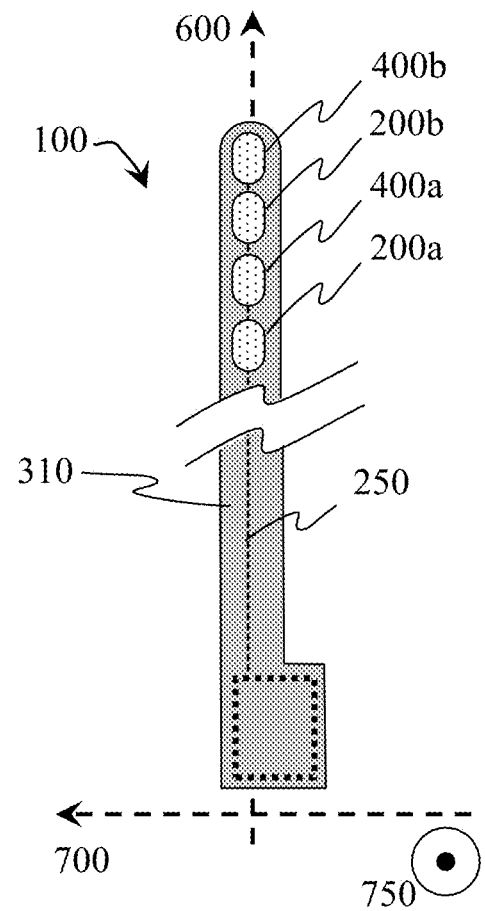
Fig. 1A
Fig. 1B
Fig. 1C

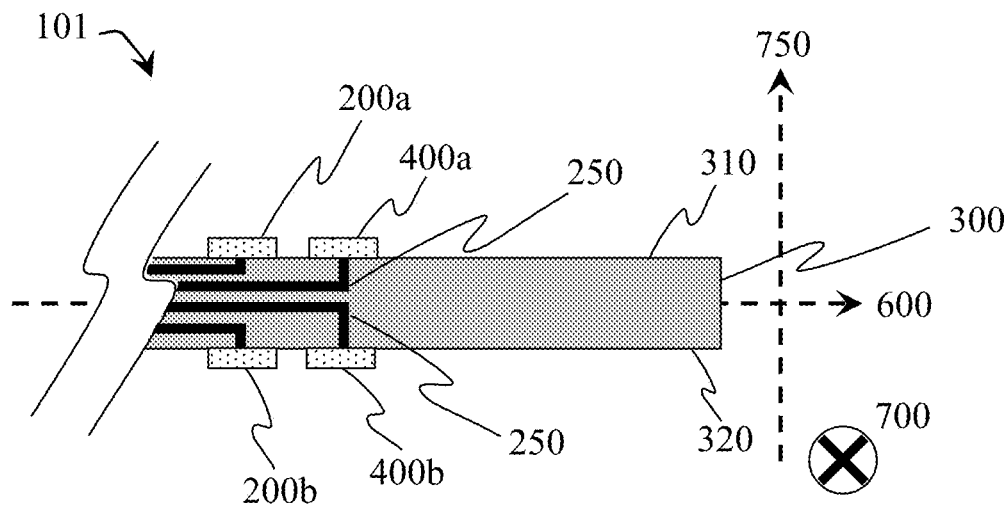
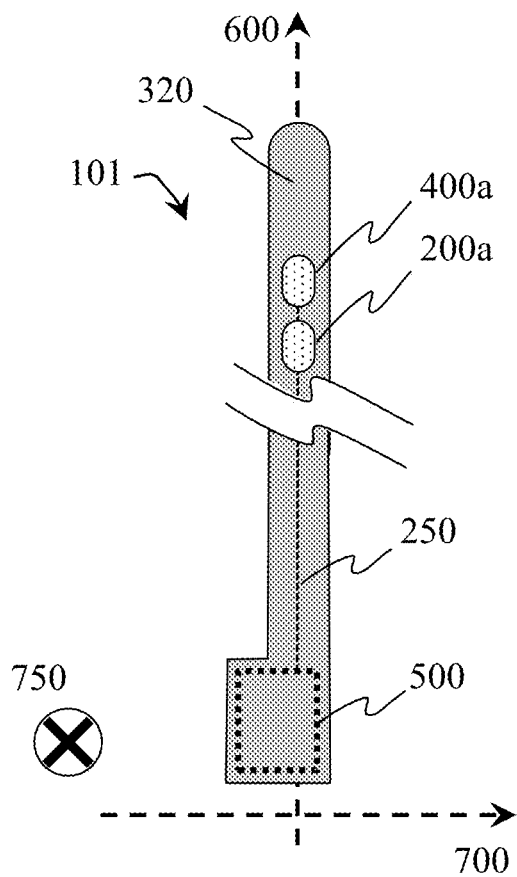
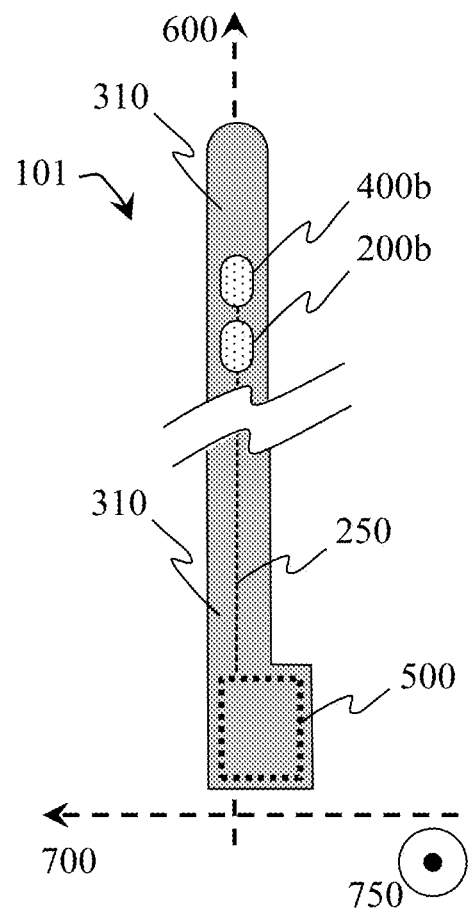
Fig. 2A
Fig. 2B
Fig. 2C

IMPLANTABLE STIMULATOR WITH A CONFORMABLE FOIL-LIKE ELECTRODE ARRAY

COPYRIGHT NOTICE

A portion of the disclosure of this patent document contains material which is subject to copyright protection. The copyright owner has no objection to the facsimile reproduction of the patent document or the patent disclosure, as it appears in the Patent and Trademark Office patent file or records, but otherwise reserves all copyright rights whatsoever.

BACKGROUND

Implantable electrical stimulation systems may be used to deliver electrical stimulation therapy to patients to treat a variety of symptoms or conditions such as headaches, lower back pain and incontinence.

In many electrical stimulation applications, it is desirable for a stimulator, typically comprising a therapeutic lead (a lead comprises electrodes and electrical connections), to provide electrical stimulation to one or more precise locations within a body—in many cases, precisely aligning the stimulation electrodes during implantation may be difficult due to the curvature of tissues and anatomical structures. A mismatch in curvature of the electrode section of a lead may create unexpected and/or unpredictable electrical resistance between one or more electrodes and the underlying tissue. In addition, repeated movement of the relevant areas of the body may even worsen the mismatch. A particular problem with subcutaneous implants is that even small differences in flexibility between the implant and surrounding tissue may affect patient comfort, and can cause irritation of the overlying skin. This is a particular problem with sub-cutaneous implants.

More recently, use has been made of plastics and polymers, which have an inherent flexibility or may be made in a curved shape—for example, as described in US application US 2016/0166828. Although such leads may be manufactured in a curved-shape or deformed by human manual manipulation during implantation, this is inconvenient. The high degree of anatomic variability found in humans and animals means that a manufacturer must provide either a large range or pre-curved leads or allow the leads to be made to measure. In the case that they are deformable during implantation, this further complicates the implantation process.

BRIEF DESCRIPTION OF THE DRAWINGS

Certain illustrative embodiments illustrating organization and method of operation, together with objects and advantages may be best understood by reference to the detailed description that follows taken in conjunction with the accompanying drawings in which:

FIG. 1A is a transverse view of a first implementation of an implantable stimulator consistent with certain embodiments of the present invention.

FIG. 1B is a top view of a first implementation of an implantable stimulator consistent with certain embodiments of the present invention.

FIG. 1C is a bottom view of a first implementation of an implantable stimulator consistent with certain embodiments of the present invention.

FIG. 2A is a transverse view of a second implementation of an implantable stimulator consistent with certain embodiments of the present invention.

FIG. 2B is a top view of a second implementation of an implantable stimulator consistent with certain embodiments of the present invention.

FIG. 2C is a bottom view of a second implementation of an implantable stimulator consistent with certain embodiments of the present invention.

DETAILED DESCRIPTION

Figure 3A:
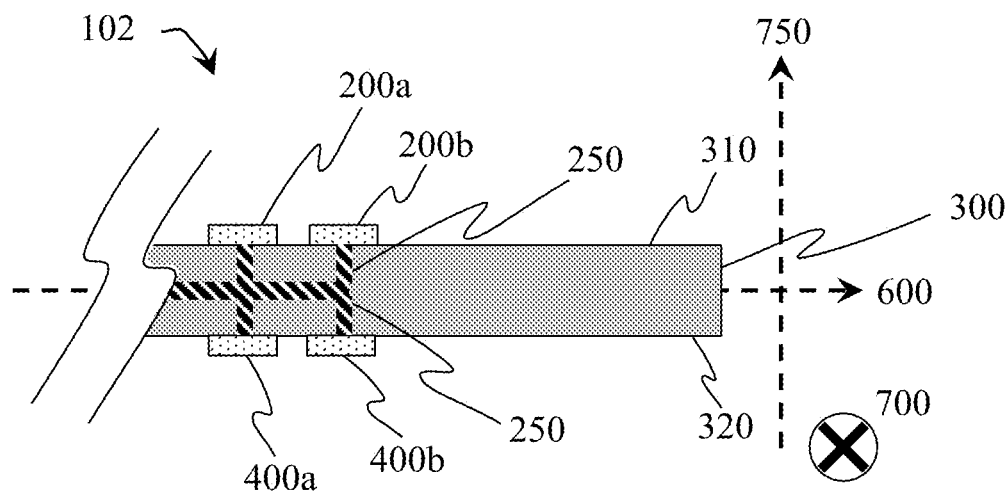
FIG. 3A is a transverse view of a third implementation of an implantable stimulator consistent with certain embodiments of the present invention.

While this invention is susceptible of embodiment in many different forms, there is shown in the drawings and will herein be described in detail specific embodiments, with the understanding that the present disclosure of such embodiments is to be considered as an example of the principles and not intended to limit the invention to the specific embodiments shown and described. In the description below, like reference numerals are used to describe the same, similar or corresponding parts in the several views of the drawings.

The terms "a" or "an", as used herein, are defined as one or more than one. The term "plurality", as used herein, is defined as two or more than two. The term "another", as used herein, is defined as at least a second or more. The terms "including" and/or "having", as used herein, are defined as comprising (i.e., open language). The term "coupled", as used herein, is defined as connected, although not necessarily directly, and not necessarily mechanically.

Reference throughout this document to "one embodiment", "certain embodiments", "an embodiment" or similar terms means that a particular feature, structure, or characteristic described in connection with the embodiment is included in at least one embodiment of the present invention. Thus, the appearances of such phrases or in various places throughout this specification are not necessarily all referring to the same embodiment. Furthermore, the particular features, structures, or characteristics may be combined in any suitable manner in one or more embodiments without limitation.

In the following detailed description, numerous non-limiting specific details are given to assist in understanding this disclosure.

FIGS. 1A, 1B & 1C depict longitudinal cross-sections through a first embodiment 100 of an implantable stimulator comprising:
  a pulse generator 500 (only depicted in FIGS. 1B and 1C) for generating one or more electrical treatment stimulation pulses; and
  a conformable foil-like substrate 300 having a longitudinal axis 600 extending from the pulse generator 500 to a distal end of the substrate 300. The substrate 300 comprises one or more adjacent polymeric substrate layers and has a first 310 and second 320 planar surface.

The implantable stimulator 100 also comprises:
  an electrode array 200, 400, proximate the distal end, having one or more electrodes of a first 200a, 200b type and one or more electrodes of a second type 400a, 400b. The electrodes 200, 400 are comprised in the first 310 or second 320 surface, and each is configurable for transferring treatment energy, in use, to (as a stimulation electrode) and/or from (as a return electrode) human or animal tissue. In this context, an array may be considered a systematic arrangement of two or more electrodes 200a, 200b, 400a, 400b. 1D, 2D or 3D arrays may be provided. Optionally, they may be arranged in rows and/or columns.

The implantable stimulator 100 further comprises:
  one or more electrical interconnections 250, between the pulse generator 500 and the first 200a, 200b and the second 400a, 400b electrodes, for transferring electrical energy as one or more electrical treatment stimulation pulses to the first electrode 200a, 200b and/or the second electrodes 400a, 400b. The one or more electrical interconnections 250 are comprised between the first surface 310 and the second 320 surfaces.

In this disclosure, the conformability of the electrode array 200, 400 is determined to a high degree by the one or more of the following:
  the conformability of the substrate 300 proximate the electrodes 200, 300;
  the arrangement and positions of the electrodes 200, 400;
  the materials and dimensions (or extent) of the materials comprised in the electrodes 200, 400;
  the arrangement and positions of the one or more interconnections 250 proximate the electrodes 200, 400; and
  the materials and dimensions (or extent) of the materials comprised in the interconnections 200, 400.

By suitable configuration, arrangement and optimization, an implantable electrode array 200, 400 may be provided which is foil-like (or film-like) and highly conformable.

As depicted, the conformable foil-like substrate 300 is preferably elongated along the longitudinal axis 600, having a tape-like shape, allowing the pulse generator 500 to be disposed further away from the position of the electrodes 200, 400.

If the substrate 300 is substantially planar (in a non-limiting example, by allowing the substrate 300 to conform to a planar surface), the first 310 and second 320 surfaces are disposed along substantially parallel transverse planes 600, 700. As depicted in FIG. 1A, the first surface 310 lies in a plane comprising the longitudinal axis 600 and a first transverse axis 700—the first transverse axis 700 is substantially perpendicular to the longitudinal axis 600. As depicted in FIG. 1A, the plane of the first surface 310 is substantially perpendicular to the plane of the cross-section drawing (substantially perpendicular to the surface of the paper).

The conformable foil-like substrate 300 has a maximum thickness of 0.5 millimeter or less, proximate the first 200a, 200b and second 400a, 400b electrodes, the thickness being determined by a perpendicular distance between corresponding points on the first 310 and second planar surfaces 320. This is preferably determined when the substrate 300 conforms to a planar surface.

The foil-like substrate 300 has a thickness or extent along a second transverse axis 750—this second transverse axis 750 is substantially perpendicular to both the longitudinal axis 600 and the first transverse axis 700—it lies in the plane of the drawing (along the surface of the paper) as depicted. The first surface 310 is depicted as an upper surface and the second surface 320 is depicted as a lower surface.

The thickness may therefore be determined by a perpendicular distance along the second transverse axis 750 between corresponding points on the first 310 and second planar surfaces 320. The maximum thickness of the conformable foil-like substrate 300 proximate the first 200a, 200b and second 400a, 400b electrodes is 0.5 mm or less, preferably 0.3 millimeters or less, even more preferably 0.2 millimeters or less, yet more preferably 0.1 millimeters or less.

In general, the lower the maximum thickness (in other words, the thinner the substrate), the higher the degree of conformance.

To clarify the differences between the different views depicted, the axes are given nominal directions:
  the longitudinal axis 600 extends from the proximal end (not depicted in FIG. 1A, but depicted in FIGS. 1B and 1C) on the left, to the distal end, depicted on the right of the page;
  the first transverse axis 700 extends into the page as depicted; and
  the second transverse axis 750 extends from bottom to top as depicted.

The conformable foil-like substrate 300 may be described as a multilayer—it comprises one or more adjacent polymeric substrate layers having the first 310 and second 320 planar surface. The one or more electrical interconnections 250 are also comprised between the first 310 and second 320 planar surfaces. However, it is not necessary that the one or more polymeric layers and/or interconnections have similar extents along the first transverse axis 700. In other words, within the context of this disclosure, there may be regions where an interconnection 250 is sandwiched between regions of polymeric substrate (appears as a multilayer in a longitudinal cross-section), adjacent to regions where the polymeric substrate is substantially contiguous. Similarly, there may be regions where an interconnection 250 is sandwiched between two polymeric substrate layers (appears as a multilayer in a longitudinal cross-section), adjacent to regions where the substrate comprises two adjacent substrate layers. Similarly, a substrate comprising two or more polymeric substrate layer may be modified (physically and/or chemically), such that it appears to be one layer of polymeric substrate.

These polymeric substrate layers are selected for suitability to be conformable, and to comprises the one or more electrical interconnections 250. Preferably, the polymeric substrate materials are also biocompatible and durable, such as a material selected from the group comprising silicone rubber, siloxane polymers, polydimethylsiloxanes, polyurethane, polyether urethane, polyetherurethane urea, polyesterurethane, polyamide, polycarbonate, polyester, polypropylene, polyethylene, polystyrene, polyvinyl chloride, polytetrafluoroethylene, polysulfone, cellulose acetate, polymethylmethacrylate, polyethylene, and polyvinylacetate. Suitable polymer materials, including LCP (Liquid Crystal Polymer) films, are described in "Polymers for Neural Implants", Hassler, Boretius, Stieglitz, Journal of Polymer Science: Part B Polymer Physics, 2011, 49, 18-33 (DOI 10.1002/polb.22169), In particular, Table 1 is included here as reference, depicting the properties of Polyimide (UBE U-Varnish-S), Parylene C (PCS Parylene C), PDMS (NuSil MED-1000), SU-8 (MicroChem SU-8 2000 & 3000 Series), and LCP (Vectra MT1300).

Conformable foil-like substrates 300 are configured to follow the contours of the underlying anatomical features very closely by being flexible. Very thin foil-like substrates 300 have the additional advantage that they have increased flexibility.

Most preferably, the polymeric substrate layers comprise an LCP, Parylene and/or a Polyimide. LCP's are chemically and biologically stable thermoplastic polymers which allow for hermetic sensor modules having a small size and low moisture penetration.

Advantageously, an LCP may be thermoformed allowing complex shapes to be provided. Very thin (and subsequently very conformable) and very flat (highly planar) layers of an LCP may be provided. For fine tuning of shapes, a suitable laser may also be used for cutting.

In a non-limiting example, a conformable foil-like substrate 300 of LCP may have a thickness (extent along the second transverse axis 750) in the range 50 microns (um) to 720 microns (um), preferably 100 microns (um) to 300 microns (um). In an exemplary embodiment, values of 150 um (micron), 100 um, 50 um, or 25 um may be provided. When conforming to a substantially planar surface, the foil-like surface 300 is substantially comprised in a plane with a transverse extent substantially perpendicular to the longitudinal axis 600, wherein the planar width may be determined by a perpendicular distance between corresponding points on outer surfaces edges of the planar foil-like substrate 300 along the transverse extent. As depicted, this is along the first transverse axis 700. In an embodiment, Electrode 200, 400 widths of 2 mm to 20 mm may be provided using LCP.

At room temperature, thin LCP films have mechanical properties similar to steel. This is important as implantable substrates 300 must be strong enough to be implanted, strong enough to be removed (explanted) and strong enough to follow any movement of the neighboring anatomical features and/or structures without deteriorating.

LCP belongs to the polymer materials with the lowest permeability for gases and water. LCP's can be bonded to themselves, allowing multilayer constructions with a homogenous structure.

In contrast to LCP's, polyimides are thermoset polymers, which require adhesives for the construction of multilayer electrode arrays. Polyimides are thermoset polymer material with high temperature and flexural endurance.

In an embodiment, an LCP may be used to provide conformable substrate 300 as a—in other words, two or more adjacent polymeric substrate layers. In a non-limiting example, these may be layers of 25 um (micron) thickness.

In an embodiment, one or more electrical interconnections 250 may be provided between the first (310) and second (320) surfaces by metallization. These may be conductors embedded in the substrate 300 such as having a single polymer layer and applying conductive material using suitable deposition techniques known from the semiconductor industry.

In an embodiment, if more than one adjacent polymeric substrate layer is provided, an interconnection layer may be provided using suitable techniques such as those from the semiconductor industry. The polymeric substrate layers may also be considered adjacent when one of more adhesion layers are used between them.

In an embodiment, lamination may also be used to provide a substrate 300 with the desired physical and chemical properties, and/or to provide a convenient method of manufacture. In a non-limiting example, a substrate 300 may comprise three laminated polymer layers: two high temperature thermoplastic layers with a low-temperature layer (bond-ply) in between, and high-temperature layers towards the first surface 310 and second surface 320.

In an alternative embodiment, two layers of silicone may be provided as polymeric substrate layers: one layer of silicone is provided, metal is patterned on one of its outer surfaces, and a second layer of silicone is added over the metal patterning by jetting, over-molding, or spin-coating.

In an embodiment, the electrical interconnections 250 may comprise one or more conductive materials, such as a metal, formed as required in one or more conductive elements: wire, strand, foil, lamina, plate, and/or sheet. They may be a substantially contiguous (one conductor). They may also comprise more than one conductor, configured and arranged to be, in use, electrically connected with each other—in other words, the one or more conductors are configured and arranged to be substantially electrically contiguous in use.

Alternatively, the one or more electrical interconnections 250 may be comprised in one or more conductive interconnection layers 250, the one or more conductive interconnection layers being comprised between two adjacent polymeric substrate layers. As depicted in FIG. 1A, a plurality of interconnections may be provided at different dispositions (or depths) between the first surface 310 and the second surface 320.

In an embodiment, an interconnection 250 in the context of this disclosure is not configured or arranged to be, in use, in contact with human or animal tissue. The one or more interconnections 250 are embedded in one or more layers of a low conductance or insulating polymer, such as LCP. Additionally or alternatively, one or more encapsulation layers may be used.

One or more interconnection layers 250 may also be provided by metallization using techniques from the PCB (Printed Circuit Board) industry, such as metallization with a bio-compatible metal such as gold or platinum. Electroplating may be used. Layers comprising LCP films are particularly suitable for metallization. These electrical interconnections 250 and/or interconnect layers 250 are configured to transfer electrical energy as one or more electrical treatment stimulation pulses from the pulse generator 500 to the first electrode 200a, 200b and/or the second electrodes 400a, 400b.

Using suitable polymeric substrate materials, such as an LCP film, allows the conformable foil-like (or film-like) substrate 300 and electrode array 200, 300 to have a high width-to-height ration, providing a bio-compatible electronic foil (or film), or bio-electronic foil (or film).

In an embodiment, when the substrate 300 conforms to a substantially planar surface, the ratio of maximum planar width to maximum thickness proximate the first 200a, 200b and second 400*a*, 400*b* electrodes may be 7:1 or higher, preferably 10:1 or higher, more preferably 15:1 or higher, yet more preferably 30:1 or higher, even more preferably 50:1 or higher.

Ratios of 100:1 or higher may also be advantageous, and may be provided using one or more mechanically strong substrate layers of an LCP film, with a width of approximately 20 mm and a thickness of approximately 0.2 mm. This provides a high degree of flexibility, and therefore also a high degree of conformability. Additional measures may also be taken to increase the degree of conformability in the first transverse direction 700, such as varying the width of the substrate, adding one or more undulations and/or providing bending points.

In a non-limiting example, when using a single row of electrodes 200, 400 and/or electrodes 200, 400 with a smaller width, the width may be four mm with a thickness of approximately 0.2 mm—this is a ratio of approximately 20:1.

In a non-limiting example, proximate the pulse generator 500, greater extents may be required which further depend, to a high degree, on the dimensions of the electronic components used a width of twenty mm and a thickness of three mm. This is a ratio of approximately 6.67:1.

As depicted in FIG. 1A, the distal end of the conformable foil-like substrate 300 comprises:
two electrodes 200*a*, 200*b* of a first type, comprised in the first surface 310, and
two electrodes 400*a*, 400*b* of a second type, also comprised in the first surface 310.
From proximal to distal end, the order depicted is 200*a*, 400*a*, 200*b*, 400*b*—in other words, each electrode of the first type 200*a*, 200*b* is proximate an electrode of the second type 400*a*, 400*b* and comprised in the same surface 310.

The foil-like substrate 300 comprises an electrical interconnection 250 between each electrode 200*a*, 400*a*, 200*b*, 400*b* and the pulse generator. In this embodiment, each electrical interconnection 250 is configured and arranged such that each electrode 200*a*, 400*a*, 200*b*, 400*b* is electrically connected substantially independently—consequently, one of the operating modes available by suitably configuring the pulse generator 500 is substantially independent operation. The pulse generator 500 may be configured using one or more hardware, firmware and/or software parameters.

Although depicted in FIG. 1A as individual connections 250 at different distances between the first 310 and second 320 surfaces, the skilled person will also realize that the same interconnections may be provided by a suitably configured interconnections 250 (or an interconnection layer 250) at approximately the same distance between the first 310 and second 320 surfaces, similar to the embodiment depicted in FIG. 3B, and described below.

"Comprised in" the first 310 or second 320 surface means that the electrodes 200*a*, 400*a*, 200*b*, 400*b* are relatively thin (such as when the substrate conforms to a substantially planar surface, having an extent along the second transverse axis of 20 to 50 microns or less. Thinner electrodes may be also be used to further increase the degree of conformability, such as 1 micron or less), and attached to (or at least partially embedded in) the surface.

The electrodes 200 may comprise a conductive material such as gold, platinum, platinum black, TiN, IrO$_2$, iridium, and/or platinum/iridium alloys and/or oxides. Conductive polymers, such as Pedot, may also be used. Preferably, bio-compatible conductive materials are used. PCB/metallization techniques may be used to attach them to the first 310 and/or second 330 surfaces of the one or more polymeric substrate layers.

Thicker metal layers are generally preferred over thinner metal layers for electrodes 200*a*, 200*b*, 400*a*, 400*b* because they can be subjected to bodily substances that may dissolve the metal. However, thicker metal layers typically increase rigidity (reduce conformability) proximate the thicker layer.

The stimulator 100 may be implanted by first creating a subcutaneous tunnel and/or using an implantation tool. However, the high degree of conformability may make successful implantation more difficult. Even when using a suitable insertion tool, the electrode positions may be found later to be incorrect due to misalignment, lead migration during implantation, or lead migration after transplantation.

At least the distal end comprising the electrode array 200, 400, is implanted. However, it may be advantageous to implant the stimulator 100.

In addition, during implantation, it may be difficult to precisely identify the desired position for the stimulation. When implanted the stimulator electrodes should be positioned sufficiently close to the nerve to be stimulated. But nerve pathways may not always be clearly visible to the professional performing the implantation, and the disposition and path of the nerve pathways vary greatly from person-to-person.

As depicted in FIG. 1, there is no substantial hardware difference between the first-type 200*a*, 200*b* and second type 400*a*, 400*b* electrodes—any difference in functionality is determined in this implementation mainly by the configuration (one or more hardware, firmware and/or software parameters) of the pulse generator 500. There may be a smaller influence on the electrical properties due to the arrangement and routing of the interconnections 250.

One or more electrodes of the same type 200*a*, 200*b* or 400*a*, 400*b* may be operated substantially the same by suitable configuration of the pulse generator 500—in other words, the stimulation energy applied to the electrodes 200, 400 is substantially the same at substantially the same time instance (usually measured as a voltage, a current, a power, a charge, or any combination thereof). This may also be used to anticipate and/or correct for a misalignment and/or lead migration—this is advantageous as it allows the configuration to be performed at least partially using software.

Additionally or alternatively, two or more electrodes 200, 400 may be configured and arranged using one or more parameters of the pulse generator 500 as a stimulation electrode or a return electrode. This may provide a higher degree of configurability as it only becomes necessary to implant the substrate 300 such that at least two of the electrodes are proximate the desired stimulation location.

In this embodiment 100, the electrodes of the first type 200*a*, 200*b* are nominally configured and arranged to be operated as a stimulation electrode.

The electrodes of the second type 400*a*, 400*b* are nominally configured to be operated as a return electrode—each is configured to provide, in use, an electrical return for one or more stimulation electrode 200*a*, 200*b*. In other words, the electrical return 400*a*, 400*b* closes the electrical circuit. It may also be similarly configured to provide an electrical ground for a corresponding electrical energy source.

Three configurations are thus provided based on this nominal configuration: either:
a stimulation/return electrode pair 200*a*/400*a* proximate the first surface 310 at that stimulation/return location; or a stimulation/return electrode pair 200b/400b proximate the first surface 310 at that stimulation/return location; or a combination thereof.

In an embodiment, one or more stimulation electrodes 200a, 200b may be provided in such a stimulator 100. The number, dimensions and/or spacings of the stimulating electrodes 200a, 200b may be selected and optimized depending on the treatment. In an embodiment, if more than one stimulation electrode 200a, 200b is provided, each stimulation electrode 200a, 200b may provide:

a different stimulation effect, a similar stimulation effect or the same stimulation effect.

To avoid a misalignment, a selection may be made of one or two electrodes 200a, 200b proximate the tissues where the effect is to be created.

Two or more stimulation electrodes 200a, 200b may be made active at substantially the same time if stimulation over a larger area is required and/or at a location between the active stimulation electrodes 200a, 200b.

In an embodiment, a stimulation electrode 200a, 200b may have dimensions in the order of six to eight mm along the longitudinal axis 600, and three to five mm along the first transverse axis 700, so approximately 18 to 40 square mm (mm$^2$).

A foil-like substrate 300, suitable for an implant, may comprise up to twelve stimulation 200a, 200b and return 400a, 400b electrodes over a length of 15 cm to allow for a correction for misalignment, or to simply allow the healthcare professional to select the most effective stimulation location.

In an embodiment, FIG. 1B depicts a view of the second surface 320 of the implantable distal end of the foil-like substrate 300 depicted in FIG. 1A. In other words, the second surface 320 is depicted in the plane of the paper, lying along the longitudinal axis 600 (depicted from bottom to top) and in the first transverse axis 700 (depicted from left to right). The second transverse axis 750 extends into the page. The first surface 310 is not depicted in FIG. 1B, but lies at a higher position along the second transverse axis 750 (into the page), and is also substantially parallel to the plane of the drawing. The foil-like substrate 300 conforms to a substantially planar surface.

The pulse generator 500 may be disposed between the second 320 surface and the first 310 surface. In FIGS. 1B and 1C, it is depicted with dotted lines. Alternatively, the pulse generator 500 may be at least partially disposed on the first surface 310 or on the second surface 320. Alternatively, the pulse generator 500 may be at least partially embedded in the first surface 310 or in the second surface 320.

Depending on the degree of embedding and the one or more electrical components used for the pulse generator 500, the maximum thickness may be optimized. Components may be thinned to minimize the thickness. By using a conformable foil-like substrate 300 as disclosed herein, the maximum thickness of the implantable stimulator 100 proximate the pulse generator 500 may be five millimeters or less, preferably four millimeters or less, even more preferably three millimeters or less, the thickness being determined by a perpendicular distance between corresponding points on outer planar surfaces when the implantable stimulator 100 conforms to a substantially planar surface. Additional optional electrical components, such as an antenna, comprising a coil or dipole or fractal antenna, may also influence the thickness depending on the degree that they are embedded in the substrate.

The stimulator 100 and the foil-like substrate 300 extend along the first transverse axis 700 (considered the planar width of the stimulator 100/foil-like substrate 300 when conforming to a substantially planar surface). As depicted, the planar width proximate the pulse generator 500 may be greater than the planar width proximate the electrodes 200a, 200b, 400a, 400b at the distal end of the foil-like substrate 300. The planar width proximate the pulse generator 500 may depend on the hardware and components used for the pulse generator 500—typically, it is at least the width of the integrated circuit used for the pulse generator 500. Additional optional electrical components, such as an antenna comprising a coil or dipole or fractal antenna, may also influence the planar width.

In an embodiment, the planar width proximate the electrodes 200a, 200b, 400a, 400b may depend on the conductors used for the electrodes 200a, 200b, 400a, 400b and the one or more interconnections 250. In an embodiment, the planar width is at least the width of the first electrode 200a, 200b or the second electrode 400a, 400b.

In an embodiment, FIG. 1C depicts a view of the first surface 310 of the implantable distal end of the foil-like substrate 300 depicted in FIGS. 1A and 1B. In other words, the first surface 310 is depicted in the plane of the paper, lying along the longitudinal axis 600 (depicted from bottom to top) and in the first transverse axis 700 (depicted from right to left). The second transverse axis 750 extends out of the page. This is the view facing the animal or human tissue which is stimulated (in use). The second surface 320 is not depicted in FIG. 1C, but lies at a lower position along the second transverse axis 750 (into the page), and is also substantially parallel to the plane of the drawing. The foil-like substrate 300 conforms to a substantially planar surface.

The one or more interconnections 250 are disposed between the first 310 surface and the second 320 surface, as depicted in FIG. 1A. In FIG. 1C, they are depicted as dotted lines, representing the interconnections 250 (or suitably configured one or more interconnection layers 250) that have been provided for each of the electrodes 200a, 200b, 400a, 400b in this embodiment. A single dotted line 250 is depicted between the pulse generator 500 and the electrodes 200, 400 to indicate, in embodiment 100, that the interconnections 250 are at approximately the same disposition along the first transverse axis 700.

As depicted in FIG. 1C, the electrodes 200a, 200b, 400a, 400b each have a longitudinal extent (length) along the longitudinal axis 600 and a transverse extent (width) along the first transverse axis 700.

Although depicted as similar, in practice, each electrode 200a, 200b, 400a, 400b may vary in shape, transverse cross-section, orientation and/or size (or extent), depending on the intended use and/or the desired degree of configurability.

After implantation of the stimulator 100, or at least of the distal end comprising the electrode array 200, 400, the pulse generator 500 may be configured and arranged to provide, in use, electrical energy to the one or more electrodes of the first type 200a, 200b with respect to the electrical return applied to the one or more electrode of the second type 400a, 400b.

The configurability of the stimulator 100 allows, before, during and/or after implantation of at least of the distal end comprising the electrode array 200, 400, the operation of the one or more electrodes 200a, 200b, 400a, 400b to be determined and/or adapted. The operation may also be reconfigured one or more times during the period that the stimulator 100 is implanted to optimize and/or prolong treatment.

In an embodiment, the pulse generator 500 may be initially configured to nominally operate 200a and 400a as respectively a stimulation/return electrode pair. After implantation of at least the distal end 200, 400, insufficient stimulation may be observed and/or measured. If it is assumed to be due to a mainly longitudinal misalignment, the pulse generator 500 may be alternatively configured, using one or more parameters, to nominally operate 200b and 400b as respectively a stimulation/return electrode pair.

The stimulator 100 may be further configured and arranged to switch the pulse generator 500 under predetermined and/or controlled conditions between these configurations. It may be convenient to further consider these configurations as a first and second electrode modes, and allow a user to select a mode as a preference and/or switch mode. Alternatively, the pulse generator 500 may switch modes under predetermined and/or controlled conditions.

Additionally or alternatively, other modes may also be provided for configuring the pulse generator 500 to operate in:
  a first electrode mode, wherein electrical stimulation energy is provided to one or more electrodes of the first type 200a, 200b as one or more electrical treatment stimulation pulses, the one or more electrodes of the second type 400a, 400b being configured to provide, in use, a corresponding electrical return for the one or more first electrodes 200a, 200b; or
  a second electrode mode, wherein to one or more electrodes of the second type 400a, 400b as one or more electrical treatment stimulation pulses, the one or more electrodes of the first type 200a, 200b being configured to provide, in use, a corresponding electrical return for the one or more second electrodes 400a, 400b.

Again, the stimulator 100 may be further configured and arranged to switch the pulse generator 500 under predetermined and/or controlled conditions between these configurations or modes. Additionally or alternatively, a user may be allowed to select a mode as a preference and/or switch mode.

The skilled person will realize that the electrodes 200a, 200b, 400a, 400b may be configured to operate in more complex configurations, such as:
  400a and 200a may be operated as respectively a stimulation/return electrode pair (reversing the original intended operation);
  400b and 200b may be operated as respectively a stimulation/return electrode pair;
  if an intermediate stimulation is preferred, two or more electrodes 200a, 200b, 400a, 400b may be operated substantially simultaneously as one or more stimulation electrodes;
  one or more electrodes 200a, 200b, 400a, 400b may be operated as one or more return electrodes;
  electrode 400a operated as a stimulation electrode, in combination with electrode 200a and electrode 200b as return electrodes;
  electrode 400a and 200b operated as a stimulation electrode, in combination with electrode 200a and electrode 400b as a return electrode.

Alternatively or additionally, the shape, orientation, transverse cross-section, and/or size (or length) of one or more stimulation electrodes may be differently configured compared to one or more return electrodes.

A number of parameters and properties may be considered when configuring and arranging the foil-like substrate 300 proximate the electrode array 200, 400 for conformability, such as:
  the transverse 700 and/or longitudinal extent 600 of the one or more electrodes 200a, 200b, 400a, 400b
  the thickness of the foil-like substrate 300, or the perpendicular distance between the first surface 310 and the second surface 320
  the materials comprised in the foil-like substrate 300, and their physical properties
  the number and extent of interconnections 250 and/or interconnection layers 250 between the first surface 310 and second surface 320.

There have been attempts to make traditional leads, such as cylindrical leads, much thinner to allow subcutaneous implantation and/or to increase comfort by flattening. But the surface area of the flattened electrodes may become disadvantageously small.

In a non-limiting example, a conventional 0.2 mm round lead with 1 cm long electrodes is estimated to result in an electrode with approximately 6 $mm^2$ electrode surface.

However, using the conformable electrode arrays described herein, a thin substrate 300 with dimensions of 0.2 mm thick, and four mm wide may be configured and arranged to provide approximately 35 $mm^2$ electrode surface in the same length. It is estimated that this may reduce impedance by a factor of approximately 35/6, and reduce power consumption by approximately 35/6.

In an embodiment, FIGS. 2A, 2B and 2C depict longitudinal cross-sections through a second embodiment 101 of an implantable stimulator. It is similar to the first embodiment 100, depicted in FIGS. 1A, 1B and 1C except:
  instead of four electrodes comprised in the first surface 310, this embodiment comprises two electrodes in the first surface 310—nominally an electrode of the first type 200a and nominally an electrode of the second type 400a. From proximal to distal end, the order depicted is 200a, 400a—in other words, an electrode of the first type 200a is proximate an electrode of the second type 400a in the first surface 310.
  the distal end of the stimulator 101 also comprises two electrodes in the second surface 320—a further electrode nominally of the first type 200b and a further electrode nominally of the second type 400b. From proximal to distal end, the order depicted is 200b, 400b—in other words, an electrode of the first type 200b is proximate an electrode of the second type 400b in the second surface 320.
  In FIG. 2B, the view of the second surface 320 depicts the two electrodes 200a, 400a comprised in that surface, and one or more interconnections 250 are depicted using a dotted line;
  In FIG. 2C, the view of the second surface 320 depicts the two electrodes 200b, 400b comprised in that surface, and one or more interconnections 250 are depicted using a dotted line;

In this embodiment 101, the electrodes of the first type 200a, 200b are nominally configured and arranged to be operated as a stimulation electrode, and the electrodes of the second type 400a, 400b are nominally configured to be operated as a return electrode.

Three main configurations are thus provided:
  a stimulation/return electrode pair 200a/400a proximate the first surface 310; or
  a stimulation/return electrode pair 200b/400b proximate the second surface 320; or a combination thereof.

This may be advantageous if it is uncertain whether the implantable distal end of the foil-like substrate 300 may be "above" or "below" the targeted tissue such as "above" or "below" a nerve. This may be determined after implantation by attempting stimulation in each nominal configuration and observing and/or measuring the presence of neural stimulation.

As discussed above, in relation to FIGS. 1A, 1B and 1C, each electrode 200a, 200b, 400a, 400b may be operated as one or more stimulation electrodes or operated as one or more return electrodes.

Figure 3B:
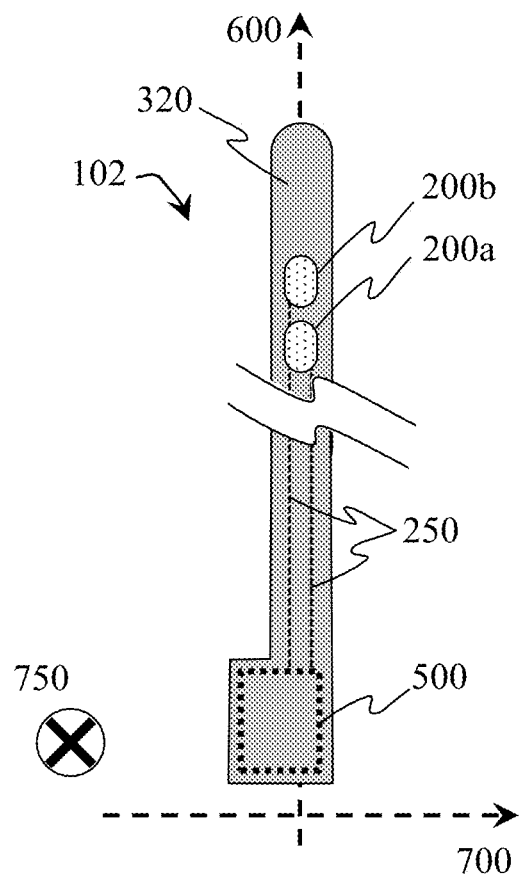
FIG. 3B is a top view of a third implementation of an implantable stimulator consistent with certain embodiments of the present invention.
Figure 3C:
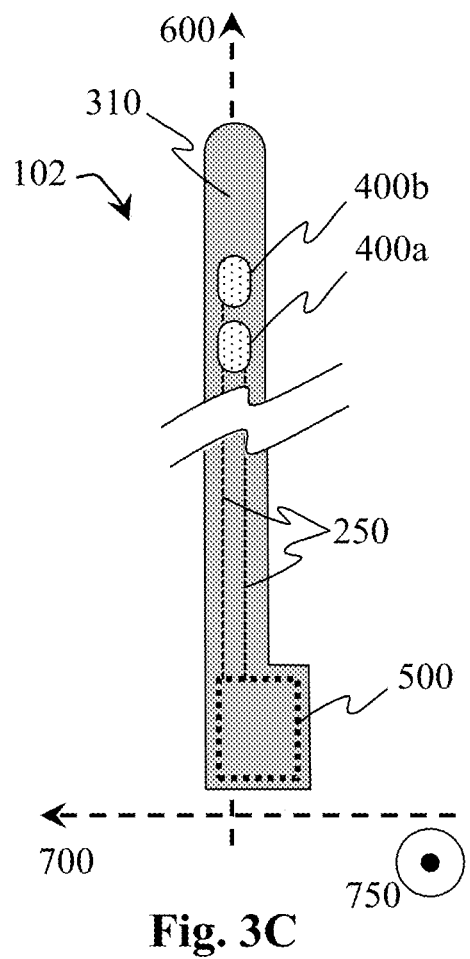
FIG. 3C is a bottom view of a third implementation of an implantable stimulator consistent with certain embodiments of the present invention.

In an embodiment, FIGS. 3A, 3B and 3C depict longitudinal cross-sections through a third embodiment 102 of an implantable stimulator. It is similar to the second embodiment 101, depicted in FIGS. 2A, 2B and 2C except:
  interconnections 250 are disposed at approximately the same disposition along the second transverse axis 750, as depicted in FIG. 3A. The lines 250 are hatched to indicate that they are not be depicted as being in the same longitudinal cross-section—there are interconnections 250 disposed at substantially different positions along the first transverse axis 700;
  interconnections 250 are disposed at substantially different dispositions along the first transverse axis 700, as depicted in FIGS. 3B and 3C as two adjacent dashed lines between the electrode array 200, 400 and the pulse generator 500;
  instead of nominally comprising an electrode of the first 200 and second type 400 in the first surface 310, the first surface 310 comprises a first 200a and second 200b electrode nominally of the first type 200;
  instead of nominally comprising an electrode of the first 200 and second type 400 in the second surface 320, the second surface 320 comprises a first 400a and second 400b electrode nominally of the second type 400;

In this embodiment 102, the electrodes of the first type 200a, 200b are nominally configured and arranged to be operated as a stimulation electrode, and the electrodes of the second type 400a, 400b are nominally configured to be operated as a return electrode.

Three main configurations are thus provided:
  a stimulation/return electrode pair 200a/400a for stimulating between the first surface 310 and second surface 320 proximate the location of this electrode pair; or
  a stimulation/return electrode pair 200b/400b for stimulating between the first surface 310 and second surface 320 proximate the location of the electrode pair; or
  a combination thereof.

This may be advantageous to correct for a longitudinal misalignment, or to simply allow the healthcare professional to select the most effective stimulation location.

As discussed above, in relation to FIGS. 2A, 2B and 2C, each electrode 200a, 200b, 400a, 400b may be operated as one or more stimulation electrodes or operated as one or more return electrodes.

Additionally or alternatively, one or more electrodes of the same type 200a, 200b or 400a, 400b may be electrically connected to each other by suitably configuring the one or more interconnections 250. They will then be operated substantially the same. This may be used to anticipate and/or correct for a misalignment and/or lead migration as longitudinal positioning is less sensitive (a stimulation is provided over a greater longitudinal and or transverse extent).

Figure 4A:
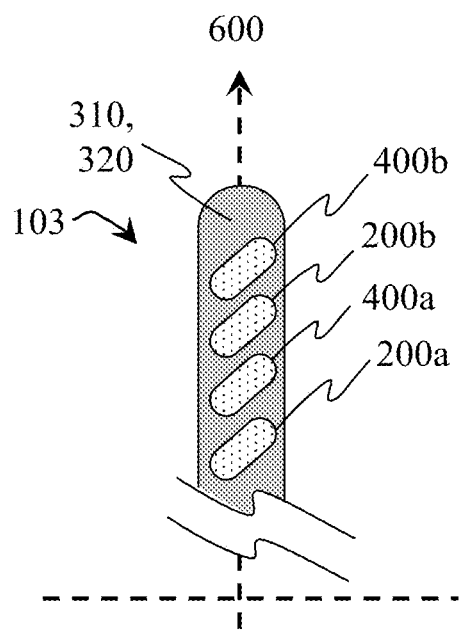
FIG. 4A is a first view of alternative electrode configurations of an implantable stimulator consistent with certain embodiments of the present invention.
Figure 4B:
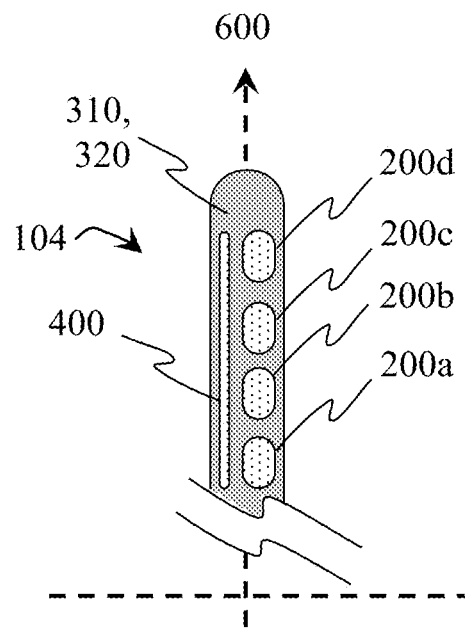
FIG. 4B is a second view of alternative electrode configurations of an implantable stimulator consistent with certain embodiments of the present invention.
Figure 4C:
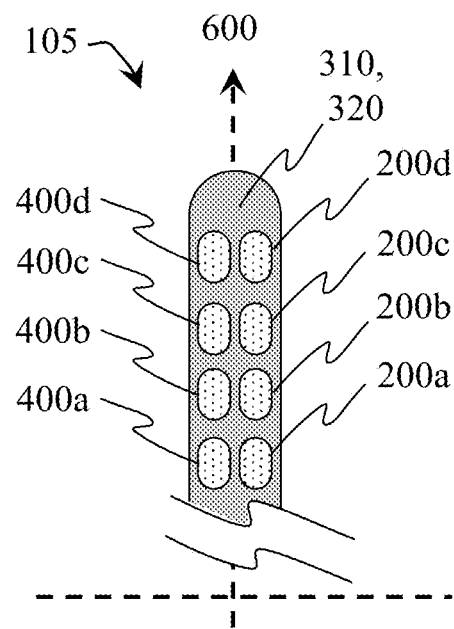
FIG. 4C is a third view of alternative electrode configurations of an implantable stimulator consistent with certain embodiments of the present invention.

FIGS. 4A, 4B and 4C depict alternative electrode array 200, 400 configurations suitable for being comprised in an implantable stimulator 100, 101, 102 as described herein.

FIG. 4A depicts an implantable distal end of a further embodiment 103 of a stimulator. Similar to the distal end depicted in FIG. 1C, the first surface 310 comprises:
  two electrodes 200a, 200b of a first type and two electrodes 400a, 400b of a second type. From proximal to distal end, the order depicted is 200a, 400a, 200b, 400b—in other words, each electrode of the first type 200a, 200b is proximate an electrode of the second type 400a, 400b and comprised in the same surface 310.

The distal end depicted in FIG. 4A is the same as that depicted in FIG. 1A, except:
  the electrodes 200, 400 are extended at angle to the longitudinal axis 600. This may reduce the sensitivity to longitudinal misalignment because the longitudinal locations over which tissue stimulation may be provided are increased.

Additionally or alternatively, the second surface 320 may similarly comprise two electrodes 200a, 200b of the first type and two electrodes 400a, 400b of the second type.

As discussed above, each electrode 200a, 200b, 400a, 400b may be operated as one or more stimulation electrodes or operated as one or more return electrodes.

FIG. 4B depicts an implantable distal end of a further embodiment 104 of a stimulator. Similar to the distal end depicted in FIG. 1C, the first surface 310 comprises four electrodes. However, in this embodiment 104, the first surface 310 comprises:
  four electrodes 200a, 200b, 200c, 200d of a first type and an electrode 400 of a second type. From proximal to distal end, the order depicted is 200a, 200b, 200c, 200d. Transversely adjacent to the four electrodes of the first type 200 is an electrode of the second type 400, extending longitudinally to be adjacent to each electrode of the first type 200.

Nominally, the electrodes of the first type 200 may be operated as one or more stimulation electrodes. The electrode of the second type 400 may be nominally operated as a return electrode for one or more of the stimulation electrodes.

This may reduce the sensitivity to longitudinal misalignment because the four different longitudinal locations are provided which may be selected for stimulation over which tissue stimulation may be provided are increased.

Additionally or alternatively, the second surface 320 may similarly comprise four electrodes 200a, 200b, 200c, 2003 of the first type and one adjacent and longitudinally extended electrode 400 of the second type.

As discussed above, each electrode 200a, 200b, 200c, 200d, 400 may be operated as one or more stimulation electrodes or operated as one or more return electrodes.

FIG. 4C depicts an implantable distal end of a further embodiment 105 of a stimulator. Similar to the distal end depicted in FIG. 4B, the first surface 310 comprises four electrodes 200a, 200b, 200c, 200d of a first type. However, in this embodiment 105, the first surface 310 further comprises four adjacent electrodes 400a, 400b, 400c, 400d of a second type. From proximal to distal end, the order depicted is 200a/400a, 200b/400b, 200c/400c, 200d/400d. Transversely adjacent to each of the four electrodes of the first type 200 is an electrode of the second type 400 at approximately the same disposition along the longitudinal axis 600.

Nominally, the electrodes of the first type 200 may be operated as one or more stimulation electrodes. The electrodes of the second type 400 may be nominally operated as a return electrode for one or more of the stimulation electrodes. Nominally, adjacent electrodes may be considered as a stimulation/return pair 200/400.

In other words, a 2×4 electrode array is provided—two along a transverse axis and four along the longitudinal axis.

This may reduce the sensitivity to longitudinal misalignment because the four different stimulation/return 200/400 pairs are provided at substantially different longitudinal locations are provided which may be selected for stimulation over which tissue stimulation may be provided are increased.

Additionally or alternatively, the second surface 320 may similarly comprise four electrodes 200a, 200b, 200c, 200d of the first type and four adjacent electrodes 400a, 400b, 400c, 400d of the second type.

As discussed above, each electrode 200a, 200b, 200c, 200d, 400a, 400b, 400c, 400d may be operated as one or more stimulation electrodes or operated as one or more return electrodes. This may also reduce the sensitivity to a transverse misalignment.

The stimulator 100, 101, 102, 103, 104, 105 may further comprise:
- an energy receiver, configured and arranged to wirelessly receive energy from an associated energy transmitter when the associated energy transmitter is proximate;
- the pulse generator 500 being further configured and arranged to receive electrical energy from the energy receiver for its operation.

Figure 5:
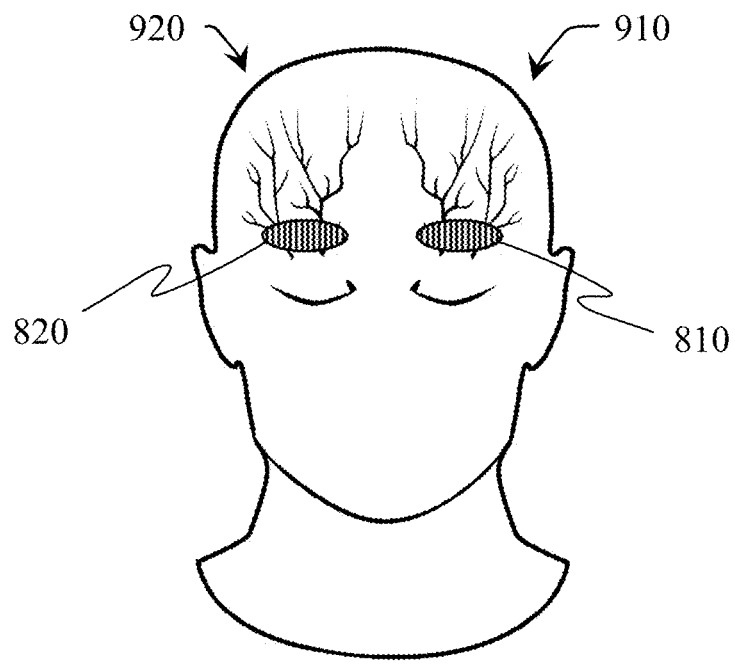
FIG. 5 presents locations of nerves in the anterior portion of a human head that may be treated through operation of an implantable stimulator consistent with certain embodiments of the present invention.
Figure 6:
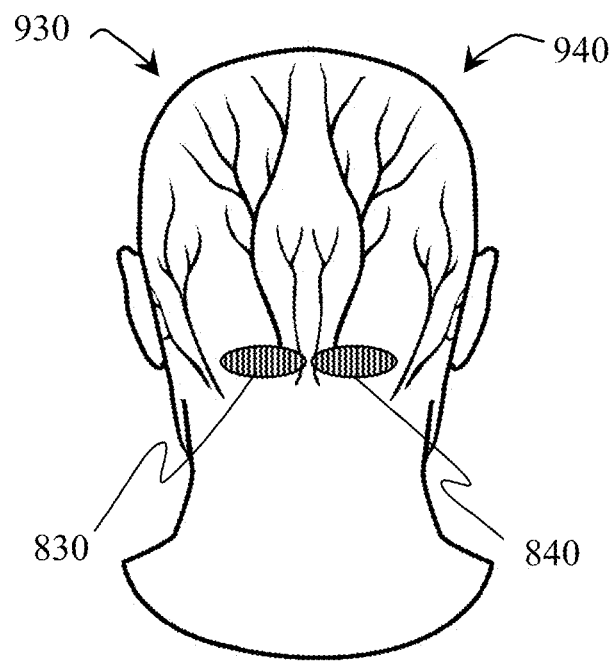
FIG. 6 presents locations of nerves in the posterior portion of a human body that may be treated through operation of an implantable stimulator consistent with certain embodiments of the present invention.

FIG. 5 and FIG. 6 depict configurations of nerves that may be stimulated using a suitably configured implantable distal end of stimulators 100, 101, 102, 103, 104, 105 to provide neurostimulation to treat conditions such as headaches or primary headaches.

FIG. 5 depicts the left supraorbital nerve 910 and right supraorbital nerve 920 which may be electrically stimulated using a suitably configured device. FIG. 6 depicts the left greater occipital nerve 930 and right greater occipital nerve 940 which may also be electrically stimulated using a suitably configured device.

Depending on the size of the region to be stimulated and the dimensions of the part of the device to be implanted, a suitable location is determined to provide the electrical stimulation required for the treatment. Approximate implant locations for the distal part of the stimulation device comprising stimulation devices 100, 101, 102, 103, 104, 105 are depicted as regions:
- location 810 for left supraorbital stimulation and location 820 for right supraorbital stimulation for treating chronic headache such as migraine and cluster.
- location 830 for left occipital stimulation and location 840 for right occipital stimulation for treating chronic headache such as migraine, cluster, and occipital neuralgia.

In many cases, these will be the approximate locations 810, 820, 830, 840 for the implantable stimulator 100, 101, 102, 103, 104, 105.

For each implant location, 810, 820, 830, 840 a separate stimulation system may be used. Where implant locations 810, 820, 830, 840 are close together, or even overlapping, a single stimulation system may be configured to stimulate at more than one implant location 810, 820, 830, 840.

A plurality of stimulation devices 100, 101, 102, 103, 104, 105 may be operated separately, simultaneously, sequentially or any combination thereof to provide the required treatment.

Figure 7:
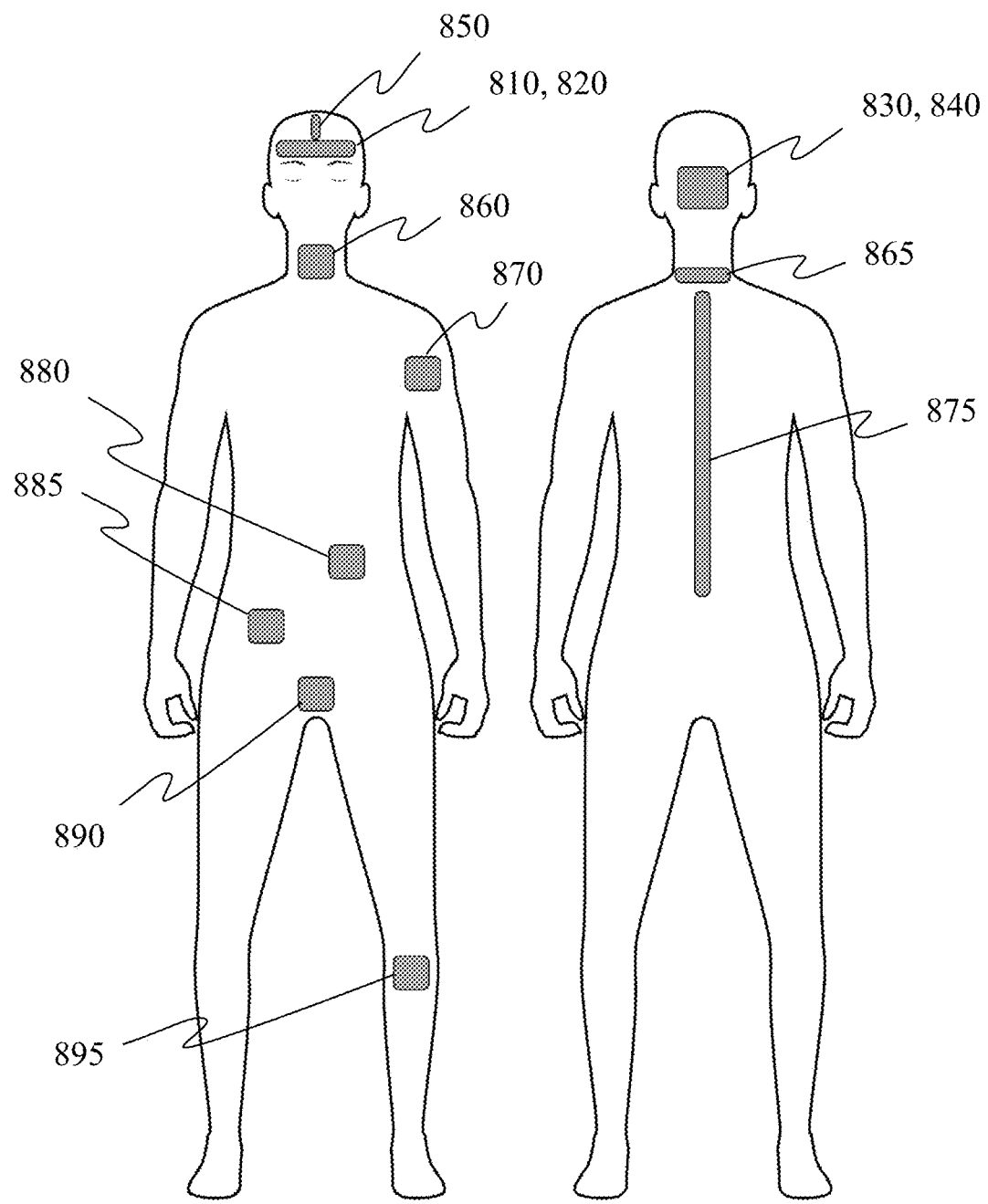
FIG. 7 presents locations of nerves in a human body that may be treated through operation of an implantable stimulator consistent with certain embodiments of the present invention.

FIG. 7 depict further configurations of nerves that may be stimulated using a suitably configured improved implantable stimulator 100, 101, 102, 103, 104, 105 to provide neurostimulation to treat other conditions. The locations depicted in FIG. 5 and FIG. 6 (810, 820, 830, 840) are also depicted in FIG. 7.

Depending on the size of the region to be stimulated and the dimensions of the part of the device to be implanted, a suitable location is determined to provide the electrical stimulation required for the treatment. Approximate implant locations for the part of the stimulation device comprising stimulation electrodes are depicted as regions:
- location 810 for cortical stimulation for treating epilepsy;
- location 850 for deep brain stimulation for tremor control treatment in Parkinson's disease patients; treating dystonia, obesity, essential tremor, depression, epilepsy, obsessive compulsive disorder, Alzheimer's, anxiety, bulimia, tinnitus, traumatic brain injury, Tourette's, sleep disorders, autism, bipolar; and stroke recovery
- location 860 for vagus nerve stimulation for treating epilepsy, depression, anxiety, bulimia, obesity, tinnitus, obsessive compulsive disorder, heart failure, Crohn's disease and rheumatoid arthritis;
- location 860 for carotid artery or carotid sinus stimulation for treating hypertension;
- location 860 for hypoglossal & phrenic nerve stimulation for treating sleep apnea;
- location 865 for cerebral spinal cord stimulation for treating chronic neck pain;
- location 870 for peripheral nerve stimulation for treating limb pain, migraines, extremity pain;
- location 875 for spinal cord stimulation for treating chronic lower back pain, angina, asthma, pain in general;
- location 880 for gastric stimulation for treatment of obesity, bulimia, interstitial cystitis;
- location 885 for sacral & pudendal nerve stimulation for treatment of interstitial cystitis;
- location 885 for sacral nerve stimulation for treatment of urinary incontinence, fecal incontinence;
- location 890 for sacral neuromodulation for bladder control treatment; and
- location 895 for fibular nerve stimulation for treating gait or footdrop.

Other conditions that may be treated include gastroesophageal reflux disease, an autoimmune disorder, inflammatory bowel disease and inflammatory diseases.

The conformability and minimum thickness of the substrate 100 and electrode array 200, 400 makes one or more implantable stimulators 100, 101, 102, 103, 104, 105 highly advantageous for the stimulation of one or more nerves, one or more muscles, one or more organs, spinal cord tissue, brain tissue, one or more cortical surface regions, one or more sulci, and any combination thereof.

The descriptions thereof herein should not be understood to prescribe a fixed order of performing the method steps described therein. Rather the method steps may be performed in any order that is practicable. Similarly, the examples used to explain the algorithm are presented as non-limiting examples, and are not intended to represent the only implementations of these algorithms. The person skilled in the art will be able to conceive many different ways to achieve the same functionality as provided by the embodiments described herein.

Many types of implantable distal ends of stimulation devices are depicted. But this does not exclude that the rest of the device is implanted. This should be interpreted as meaning that at least the electrode section of the distal end is preferably configured and arranged to be implanted.

Although the present invention has been described in connection with specific exemplary embodiments, it should be understood that various changes, substitutions, and alterations apparent to those skilled in the art can be made to the disclosed embodiments without departing from the spirit and scope of the invention as set forth in the appended claims.

In a non-limiting example,
one or more electrodes of the first type 200*a*, 200*b* are comprised in the first surface 310 and one or more electrodes of the second type 400*a*, 400*b* are comprised in the second surface 320; or
one or more electrodes of the first type 200*a*, 200*b* are comprised in the first surface 310 and one or more electrodes of the second type 400*a*, 400*b* are also comprised in the first surface 310; or
one or more electrodes of the first type 200*a*, 200*b* are comprised in the second surface 320 and one or more electrodes of the second type 400*a*, 400*b* are comprised in the first surface 310; or
one or more electrodes of the first type 200*a*, 200*b* are comprised in the second surface 320 and one or more electrodes of the second type 400*a*, 400*b* are also comprised in the second surface 320; or
any combination thereof.

The stimulator 100, 101, 102, 103, 104, 105 may be further modified. In a non-limiting example:
the foil-like substrate 300 and pulse generator 500 may be embedded in one or more flexible bio-compatible encapsulation layers. These layers may comprise: a Liquid Crystal Polymer (LCP), a Polydimethylsiloxane (PDMS), a silicone polyurethane, a Polyimide, a parylene, a biocompatible polymer, a biocompatible elastomer, and any combination thereof.

By providing relatively larger higher electrode 200, 400 surfaces, stimulators 100, 101, 102, 103, 104, 105 may be operated at a lower energy/lower power. This may be advantageous in applications where high frequency and/or burst stimulation is used.

High frequency operation may require more energy to be provided by the pulse generator 500. In applications where energy/power is critical, such as, in a non-limiting example, if an increased operating lifetime is desired from a power source for the pulse generator 500, any reduction in required power may be advantageous. High frequency operation may be considered as generating electrical stimulation pulses with a frequency of 1000 Hz or more, preferably 1500 Hz or more, more preferably 2000 Hz or more, yet more preferably 2500 Hz or more.

In an embodiment, experiments with burst stimulation have been performed such as Burst Occipital Nerve Stimulation for Chronic Migraine and Chronic Cluster Headache by Garcia-Ortega et al, Neuromodulation 2019; 22: 638-644, DOI: 10.1111/ner.12977.

For burst operation, the pulse generator 500 is further configured and arranged to generate electrical stimulation pulses in groups of stimulation pulses.

In a non-limiting example, groups (or bursts) of stimulation pulses may comprise 2 to 10 pulses, more preferably 2 to 5 stimulation pulses. Stimulation pulses in a group may have a repetition frequency of more than 500 Hz, typically 1000 Hz or more. Groups may be repeated at more than 5 Hz, typically 40 Hz or more.

As with high frequency operations, burst operation may require more energy to be provided by the pulse generator 500, and any reduction in required power may be advantageous.

Additionally, the speed of charge-balance recovery may also increase with a lower impedance. By using a relatively thin-foil substrate 300, stimulation between an electrode of the first type 200 comprised in one surface 310, 320 and an electrode of the second type 400 comprised in the other surface 310, 320, the current path in tissue is relatively short, reducing impedance.

Similarly, using a substrate 300, and stimulation between an electrode of the first type 200 comprised in one surface 310, 320 and an adjacent electrode of the second type 400 comprised in the same surface 310, 320, provide a relatively short path through tissue.

While certain illustrative embodiments have been described, it is evident that many alternatives, modifications, permutations and variations will become apparent to those skilled in the art in light of the foregoing description.

What is claimed is:

1. An implantable stimulator comprising:
a pulse generator for generating one or more electrical treatment stimulation pulses;
a conformable foil-like substrate, having a longitudinal axis extending from the pulse generator to a distal end of the substrate, the substrate comprising one or more adjacent polymeric substrate layers, the substrate having a first and second planar surface;
an electrode array, proximate the distal end, having a first and second electrode comprised in the first or second surface, each electrode in operation being configurable for transferring treatment energy to and/or from human or animal tissue;
the implantable stimulator further comprising:
one or more electrical interconnections, between the pulse generator and the first and the second electrodes, for transferring electrical energy as one or more electrical treatment stimulation pulses to the first electrode and/or the second electrodes;
where the one or more electrical interconnections are comprised between the first and second surfaces, and the conformable foil-like substrate has a maximum thickness of 0.5 millimeter or less, proximate the first and second electrodes, the thickness being determined by a perpendicular distance between corresponding points on the first and second outer planar surfaces, and
wherein the substrate and pulse generator are embedded in one or more flexible biocompatible encapsulation layers comprising Polydimethylsiloxane (PDMS).

2. The stimulator according to claim 1, where the maximum thickness of the substrate proximate the first and second electrodes is 0.3 millimeters or less, even more preferably 0.2 millimeters or less, yet more preferably 0.1 millimeters or less.

3. The stimulator according to claim 1, where the maximum thickness of the implantable stimulator proximate the pulse generator is 5 millimeters or less, preferably 4 millimeters or less, even more preferably 3 millimeters or less, the thickness being determined by a perpendicular distance between corresponding points on outer planar surfaces.

4. The stimulator according to claim 1, where:
the substrate has a surface comprised in a plane with a transverse extent substantially perpendicular to the longitudinal axis;
where the distal end of the substrate has a maximum planar width, the width being determined by a perpendicular distance between corresponding points on outer surfaces edges of the substrate along the transverse extent; and
where the ratio of maximum planar width to maximum thickness proximate the first and second electrodes being 7:1 or higher, preferably 10:1 or higher, more preferably 15:1 or higher, yet more preferably 30:1 or higher, even more preferably 50:1 or higher.

5. The stimulator according to claim 1, where the pulse generator is further configured to operate in:
- a first electrode mode, where electrical stimulation energy is provided to the first electrode as one or more electrical treatment stimulation pulses, the second electrode being configured to provide, in use, a corresponding electrical return for the first electrode; or
- a second electrode mode, wherein electrical stimulation energy is provided to the second electrode as one or more electrical treatment stimulation pulses, the first electrode being configured to provide a corresponding electrical return for the second electrode during operation;
- the stimulator being further configured and arranged to switch the pulse generator under predetermined and/or controlled conditions between the first and second electrode modes.

6. The stimulator according to claim 1, where:
- the first electrode is comprised in the first surface and the second electrode is comprised in the second surface; and/or
- the first electrode is comprised in the first surface and the second electrode is comprised in the first surface; and/or
- the first electrode is comprised in the second surface and the second electrode is comprised in the first surface; and/or
- the first electrode is comprised in the second surface and the second electrode is comprised in the second surface; and/or
- any combination thereof.

7. The stimulator according to claim 1, wherein two or more electrodes are configurable using one or more parameters of the pulse generator as a stimulation electrode or a return electrode.

8. The stimulator according to claim 1, where the stimulator further comprises:
- an energy receiver, configured and arranged to wirelessly receive energy from an associated energy transmitter when the associated energy transmitter is proximate;
- the pulse generator being further configured and arranged to receive electrical energy from the energy receiver for its operation.

9. The stimulator according to claim 1, where the substrate comprises one or more layers of a Liquid Crystal Polymer (LCP) film.

10. The stimulator according to claim 1, where the pulse generator is comprised between the first and second planar surfaces.

11. The stimulator according to claim 1, where the substrate and pulse generator are embedded in one or more flexible bio-compatible encapsulation layers.

12. The stimulator according to claim 11, where the one or more encapsulation layers further comprise a Liquid Crystal Polymer (LCP), a Polydimethylsiloxane (PDMS), a silicone polyurethane, a Polyimide, a parylene, a biocompatible polymer, a biocompatible elastomer, and any combination thereof.

13. The stimulator according to claim 1, where the pulse generator is further configured and arranged to generate electrical stimulation pulses with a frequency of 1000 Hz or more, preferably 1500 Hz or more, more preferably 2000 Hz or more, yet more preferably 2500 Hz or more.

14. The stimulator according to claim 1, where the pulse generator is further configured and arranged to generate electrical stimulation pulses in groups of stimulation pulses.

15. The stimulator according to claim 14, where the groups of stimulation pulses comprise 2 to 10 pulses, more preferably 2 to 5 stimulation pulses.

16. The stimulator according to claim 1, where the one or more electrical interconnections are comprised in one or more conductive interconnection layers, the one or more conductive interconnection layers being comprised between two adjacent polymeric substrate layers.

17. The stimulator according to claim 1 when in operation stimulating one or more nerves, one or more muscles, one or more organs, spinal cord tissue, brain tissue, one or more cortical surface regions, one or more sulci, and any combination thereof.

18. The stimulator according to claim 1 operational to treat headaches, primary headaches, incontinence, occipital neuralgia, sleep apnea, hypertension, gastro-esophageal reflux disease, an inflammatory disease, limb pain, leg pain, back pain, lower back pain, phantom pain, chronic pain, epilepsy, an overactive bladder, poststroke pain, obesity, an autoimmune disorder, rheumatoid arthritis, inflammatory bowel disease, Crohn's disease, and any combination thereof.

19. The stimulator according to claim 1 wherein the pulse generator is at least partially disposed on the first planar surface or on the second planar surface.

20. The stimulator according to claim 1 further comprising one or more adhesion layers adjacent to the one or more adjacent polymeric substrate layers.

21. An implantable stimulator comprising:
- a pulse generator for generating one or more electrical treatment stimulation pulses;
- a conformable foil-like substrate, having a longitudinal axis extending from the pulse generator to a distal end of the substrate, the substrate comprising one or more adjacent polymeric substrate layers, the substrate having a first and second planar surface;
- an electrode array, proximate the distal end, having a first and second electrode comprised in the first or second surface, each electrode in operation being configurable for transferring treatment energy to and/or from human or animal tissue;
- the implantable stimulator further comprising:
- one or more electrical interconnections, between the pulse generator and the first and the second electrodes, for transferring electrical energy as one or more electrical treatment stimulation pulses to the first electrode and/or the second electrodes;
- wherein the one or more electrical interconnections are comprised between the first and second surfaces, and the conformable foil-like substrate has a maximum thickness of 0.5 millimeter or less, proximate the first and second electrodes, the thickness being determined by a perpendicular distance between corresponding points on the first and second outer planar surfaces, and
- wherein the one or more electrical interconnections are positioned such that a conformable LCP (Liquid Crystal Polymer) area of the substrate is directly between the one or more electrical interconnections and the first outer planar surface, and directly between the one or more electrical interconnections and the second outer planar surface.

* * * * *